United States Patent
Bae et al.

(10) Patent No.: US 11,006,900 B2
(45) Date of Patent: May 18, 2021

(54) METHOD AND SYSTEM FOR STANDARDIZING HEMODYNAMICS MEASUREMENT RESULT, AND NON-TRANSITORY COMPUTER-READABLE RECORDING MEDIUM

(71) Applicant: KOREA ADVANCED INSTITUTE OF SCIENCE AND TECHNOLOGY, Daejeon (KR)

(72) Inventors: Hyeon Min Bae, Daejeon (KR); Gun Pil Hwang, Daejeon (KR); Min Gyu Choi, Daejeon (KR); Jong Kwan Choi, Daejeon (KR); Jae Myoung Kim, Daejeon (KR); Min Su Ji, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 121 days.

(21) Appl. No.: 16/324,639

(22) PCT Filed: Jul. 5, 2017

(86) PCT No.: PCT/KR2017/007179
§ 371 (c)(1),
(2) Date: Mar. 15, 2019

(87) PCT Pub. No.: WO2018/030644
PCT Pub. Date: Feb. 15, 2018

(65) Prior Publication Data
US 2019/0192081 A1    Jun. 27, 2019

(30) Foreign Application Priority Data
Aug. 10, 2016 (KR) .................. 10-2016-0101742

(51) Int. Cl.
*G06T 7/73* (2017.01)
*A61B 5/00* (2006.01)
(Continued)

(52) U.S. Cl.
CPC ............. *A61B 5/721* (2013.01); *A61B 5/00* (2013.01); *A61B 5/0042* (2013.01);
(Continued)

(58) Field of Classification Search
CPC ......... A61B 5/721; A61B 5/00; A61B 5/1455; A61B 5/684; A61B 5/4064; A61B 5/0042; A61B 5/0077; A61B 5/026; A61B 5/7253; A61B 5/6803; A61B 5/02028; A61B 5/0075; A61B 5/742; G06T 7/73
See application file for complete search history.

(56) References Cited

U.S. PATENT DOCUMENTS 6,647,146 B1 * 11/2003 Davison .................. G06T 7/564
382/199

FOREIGN PATENT DOCUMENTS

JP    2006-122086 A    5/2006
JP    2009-261588 A    11/2009
(Continued)

OTHER PUBLICATIONS

English translation of JP2012157624. (Year: 2012).*
(Continued)

*Primary Examiner* — Phuoc Tran
(74) *Attorney, Agent, or Firm* — Dinsmore & Shohl LLP; Yongsok Choi, Esq.

(57) ABSTRACT

The present disclosure relates to a method and a system for standardizing a hemodynamics measurement result and a non-transitory computer-readable recording medium. According to one aspect of the present disclosure, provided is a method for standardizing a measurement result obtained from a device for monitoring hemodynamics, the method comprising the steps of: capturing an image of a subject
(Continued)

wearing a monitoring device; defining a photogrammetric coordinate system on the captured image, and converting a preset local coordinate system on the monitoring device into the photogrammetric coordinate system; and converting the photogrammetric coordinate system into a standard coordinate system which is based on a standard space.

9 Claims, 6 Drawing Sheets

(51) Int. Cl.
*A61B 5/1455* (2006.01)
*A61B 5/026* (2006.01)
*A61B 5/02* (2006.01)

(52) U.S. Cl.
CPC ............ *A61B 5/0077* (2013.01); *A61B 5/026* (2013.01); *A61B 5/1455* (2013.01); *A61B 5/4064* (2013.01); *A61B 5/6803* (2013.01); *A61B 5/684* (2013.01); *A61B 5/7253* (2013.01); *G06T 7/73* (2017.01); *A61B 5/02028* (2013.01)

(56) References Cited

FOREIGN PATENT DOCUMENTS

| JP | 2012-157624 A | 8/2012 |
|----|---------------|--------|
| JP | 2015-115724 A | 6/2015 |
| KR | 10-2011-0006032 A | 1/2011 |

OTHER PUBLICATIONS

English translation of JP2015115724. (Year: 2015).*
International Search Report for PCT/KR2017/007179 dated Nov. 8, 2017.
Sarah Lloyd-Fox, et al., "Coregistering Functional Near-Infrared Spectroscopy With Underlying Cortical Areas in Infants", Journal Neurophotonics, Sep. 8, 2014, vol. 1, No. 2, 1000 20th St. Bellingham WA, 98225 USA.
Daisuke Tsuzuki, et al., "Spatial Registration for Functional Near-Infrared Spectroscopy: From Channel Position On the Scalp to Cortical Location in Individual and Group Analyses", Journal Neuroimage, Jan. 1, 2014, vol. 85, pp. 92-103, Amsterdam, NL.
SeN Wong, "A Fast Webcam Photogrammetric System to Support Optical Imaging Brain Activity", Thesis, Feb. 1, 2012, Department of Civil, Environmental and Geomatic Engineering, University College London.
Simone Cutini, et al., "A New Method Based on ICBM152 Head Surface for Probe Placement in Multichannel fNIRS", Journal Neuroimage, Jan. 1, 2011, vol. 54, No. 2, pp. 919-927, Amsterdam, NL.
Daisuke Tsuzuki, et al., "Virtual Spatial Registration of Stand-Alone fNIRS Data to MNI Space", Journal Neuroimage, Feb. 1, 2007, vol. 34, No. 4, pp. 1506-1518, Amsterdam, NL.
Archana K. Singh, et al., "Spatial Registration of Multichannel Multi-Subject fNIRS Data to MNI Space Without MRI", Journal Neuroimage, Oct. 1, 2005, vol. 27, No. 4, pp. 842-851, Amsterdam, NL.

* cited by examiner

FIB. 1B

Front View

Side View $$X_{Photo \to MNI-p} = M_{AT,ave} * X_{Photo-p}$$

METHOD AND SYSTEM FOR STANDARDIZING HEMODYNAMICS MEASUREMENT RESULT, AND NON-TRANSITORY COMPUTER-READABLE RECORDING MEDIUM

CROSS-REFERENCE TO RELATED APPLICATION(S)

This application is a continuation application of Patent Cooperation Treaty (PCT) international application Serial No. PCT/KR2017/007179, filed on Jul. 5, 2017, which claims priority to Korean Patent Application Serial No. 10-2016-0101742, filed on Aug. 10, 2016. The entire contents of PCT international application Serial No. PCT/KR2017/007179, and Korean Patent Application Serial No. 10-2016-0101742 are hereby incorporated by reference.

FIELD OF THE INVENTION

The present disclosure relates to a method, a system, and a non-transitory computer-readable recording medium for standardizing a hemodynamics measurement result, and more particularly to a method, a system, and a non-transitory computer-readable recording medium for standardizing a measurement result obtained from a device for monitoring hemodynamics.

BACKGROUND

Near-infrared spectroscopy (NIRS) is a method of measuring attenuation of near-infrared light (resulting from scattering and absorption due to oxidized hemoglobin or non-oxidized hemoglobin) changed according a variation in hemodynamics (e.g., concentration of the oxidized hemoglobin and the non-oxidized hemoglobin) due to activity in a body part of a person (e.g., the brain), thereby indirectly analyzing the activity in the body part. A case, as an example, of monitoring a variation in hemodynamics according to neural activity occurring in the brain will be described in detail below. A near-infrared spectrum having a wavelength in the range of about 630 nm to about 1300 nm passes through a human skull to reach a depth in the range of about 1 cm to about 3 cm from the human skull. Consequently, a variation in hemodynamics (e.g., an oxygen concentration (i.e., oxidized hemoglobin) in blood and the like) can be monitored by irradiating near-infrared light onto a human head and detecting the near-infrared light reflected or scattered therefrom.

According to recently introduced NIRS, a near-infrared light irradiation module or a near-infrared light detection module referred to as an optical sensor (optode) is arranged at various parts of a human head at a predetermined interval, and a signal related to hemodynamics (e.g., an optical density (OD) signal based on NIRS), which is acquired from the optodes, is analyzed such that it is possible to quantify neural activity in the human brain (particularly, the cortex).

As a device for monitoring a variation in hemodynamics due to brain activity using NIRS, a headset type monitoring device configured to be worn to allow optodes to be disposed adjacent to a human head.

Meanwhile, an external shape of a head surrounding the brain, i.e., a shape of the head, may be different according to a subject wearing the headset type monitoring device so that the headset type monitoring device may be installed in a different form according to the subject. For example, when a monitoring device is worn, declination of the monitoring device from a front side to a rear side of a head may be different, and thus a relative position of an optode installed at the monitoring device may also be varied.

Further, in addition to the shape of the head, an anatomical structure, i.e., a shape and a position of brain tissue according to a person may be different.

Owing to the above-described reasons, even though the same monitoring device is used, brain tissue onto which near-infrared light is irradiated and from which the near-infrared light is reflected or scattered may be different. Consequently, even though the same monitoring device is used, there is a problem in the results from different subjects cannot be compared and evaluated. Further, there is a limitation in accumulating and utilizing the results obtained through the monitoring device.

SUMMARY OF THE INVENTION

An objective of the present disclosure is to solve the above-described problems.

Further, the present disclosure is directed to providing a method, a system, and a non-transitory computer-readable recording medium for standardizing measured results of hemodynamics, which are capable of comparing the measured results with respect to different subjects and accumulating and utilizing data by mapping, when a subject wears a monitoring device, the measured results through photogrammetry in a state of wearing the monitoring device to a standard coordinate system.

A typical configuration of the present disclosure for achieving the above-described objectives is as follows.

According to one aspect of the present disclosure, provided is a method for standardizing a measurement result obtained from a device for monitoring hemodynamics, the method comprising the steps of: capturing an image of a subject wearing a monitoring device; defining a photogrammetric coordinate system on the captured image, and transforming a predetermined local coordinate system on the monitoring device into the photogrammetric coordinate system; and transforming the photogrammetric coordinate system into a standard coordinate system which is based on a standard space.

According to another aspect of the present disclosure, provided is a system for standardizing a measured result obtained from a device for monitoring hemodynamics, the system comprising an image management unit configured to receive and analyze an image of a subject wearing a monitoring device, and a coordinate management unit configured to transform a local coordinate system in the monitoring device into a photogrammetric coordinate system on the basis of the image analyzed in the image management unit and transform the photogrammetric coordinate system into a standard coordinate system again so as to map a measured result in the monitoring device to the standard coordinate system based on a standard space.

In addition to the foregoing, there are provided another method for implementing the present disclosure, another system, and a non-transitory computer-readable recording medium for recording a computer program for performing another method.

In accordance with one aspect of the present disclosure, data measured from a monitoring device using an image, which is obtained from the monitoring device worn on a subject, is mapped to a standard coordinate system based on a standard space such that measured results can standardized. Therefore, it is possible to easily evaluate measured results by directly comparing the results measured from different subjects on a standard coordinate system and to utilize big data analysis by accumulating monitored results of hemodynamics.

BRIEF DESCRIPTION OF THE DRAWINGS

FIG. 1B is a schematic diagram illustrating an external configuration of a monitoring device according to one embodiment of the present disclosure.

DETAILED DESCRIPTION

Figure 1A:
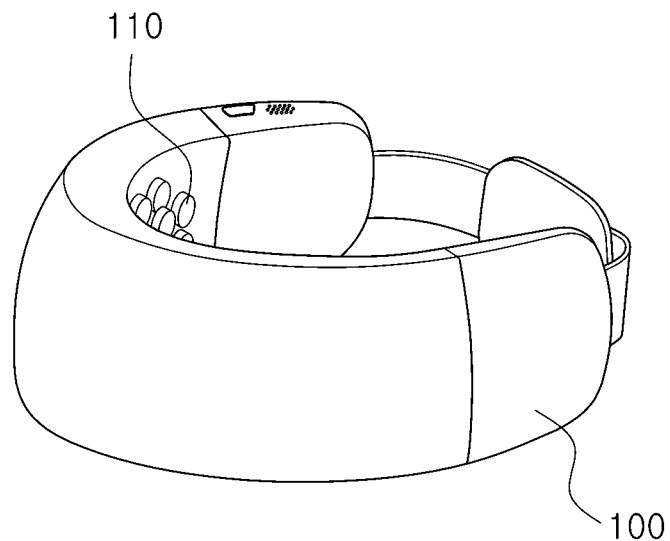
FIG. 1A is a schematic diagram illustrating an external configuration of a monitoring device according to one embodiment of the present disclosure.

In the following detailed description, reference is made to the accompanying drawings that illustrates, by way of illustration, specific embodiments in which the present disclosure may be practiced. These embodiments are described in sufficient detail to enable those skilled in the art to practice the present disclosure. It should be understood that various embodiments of the present disclosure, although different, are not necessarily mutually exclusive. For example, specific forms, structures, and characteristics described herein in connection with one embodiment may be implemented within other embodiments without departing from the spirit and scope of the present disclosure. Further, it should be understood that the location or arrangement of individual elements within each disclosed embodiment may be modified without departing from the scope of the present disclosure. The following detailed description, therefore, is not to be taken in a limiting sense, and the scope of the present disclosure is defined only by the appended claims, appropriately interpreted, along with the full range of equivalents to which the claims are entitled. In the drawings, similar numerals refer to the same or similar functionality throughout the several views.

Hereinafter, exemplary embodiments of the present disclosure will be described in detail with reference to the accompanying drawings so as to enable those skilled in the art to which the present disclosure pertains to practice the present disclosure.

In this disclosure, components in blood (e.g., an oxyhemoglobin concentration, a deoxyhemoglobin concentration, oxygen saturation in blood, and the like), a blood flow rate, a blood volume, and the like may be included in hemodynamics which will be a target of monitoring performed by a monitoring device and a monitoring system.

Configuration of Monitoring Device

Figure 1A:
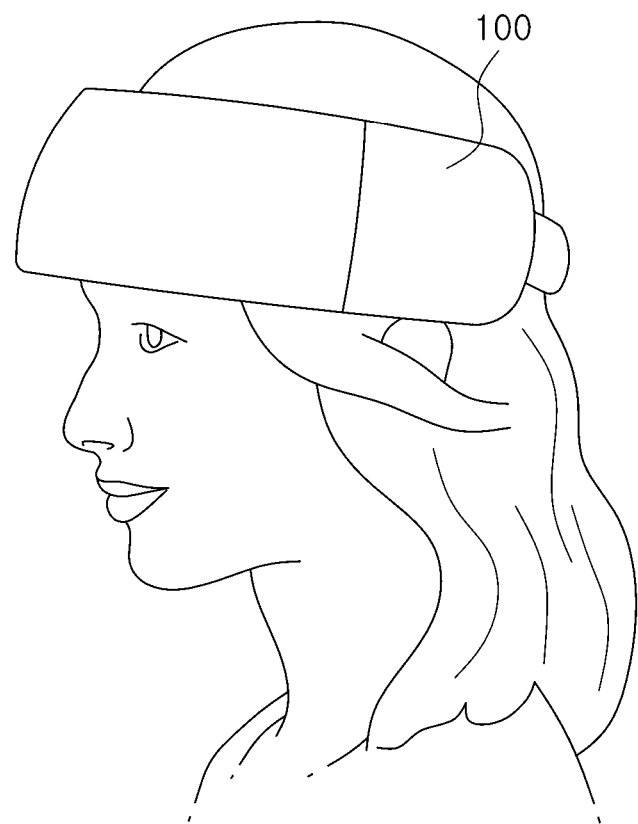

FIG. 1 is a schematic diagram illustrating an external configuration of a monitoring device according to one embodiment of the present disclosure.

Referring to FIG. 1, a monitoring device 100 according to one embodiment of the present disclosure may be worn on a body part (e.g., a head part or the like) of a subject (see FIG. 1B), and the monitoring device 100 may perform a function of measuring a predetermined signal from the subject and a function of monitoring activity in the corresponding body part of the subject (e.g., neural activity and the like occurring in the brain) by processing or analyzing the measured signal.

Specifically, the monitoring device 100 according to one embodiment of the present disclosure may include plurality of optodes 110, each performing a function of irradiating near-infrared light onto a head portion of the subject and detecting the near-infrared light reflected or scattered from the head portion (more specifically, cerebral venous blood) of the subject (see FIG. 1A). For example, signals measured by the plurality of optodes 110, which are included in the monitoring device 100 according to one embodiment of the present disclosure, may be optical density (OD) signals based on near-infrared spectroscopy.

Configuration of Monitoring System

An internal configuration and a function of each component of the monitoring system performing an important function for implementation of the present disclosure will be described below. Meanwhile, the monitoring system in the present disclosure corresponds to a system for standardizing results measured by the monitoring device, and throughout this disclosure, the monitoring system is used in the same meaning as a system for standardizing results measured by a device for monitoring hemodynamics or as a system for standardizing measured hemodynamics results.

Figure 2:
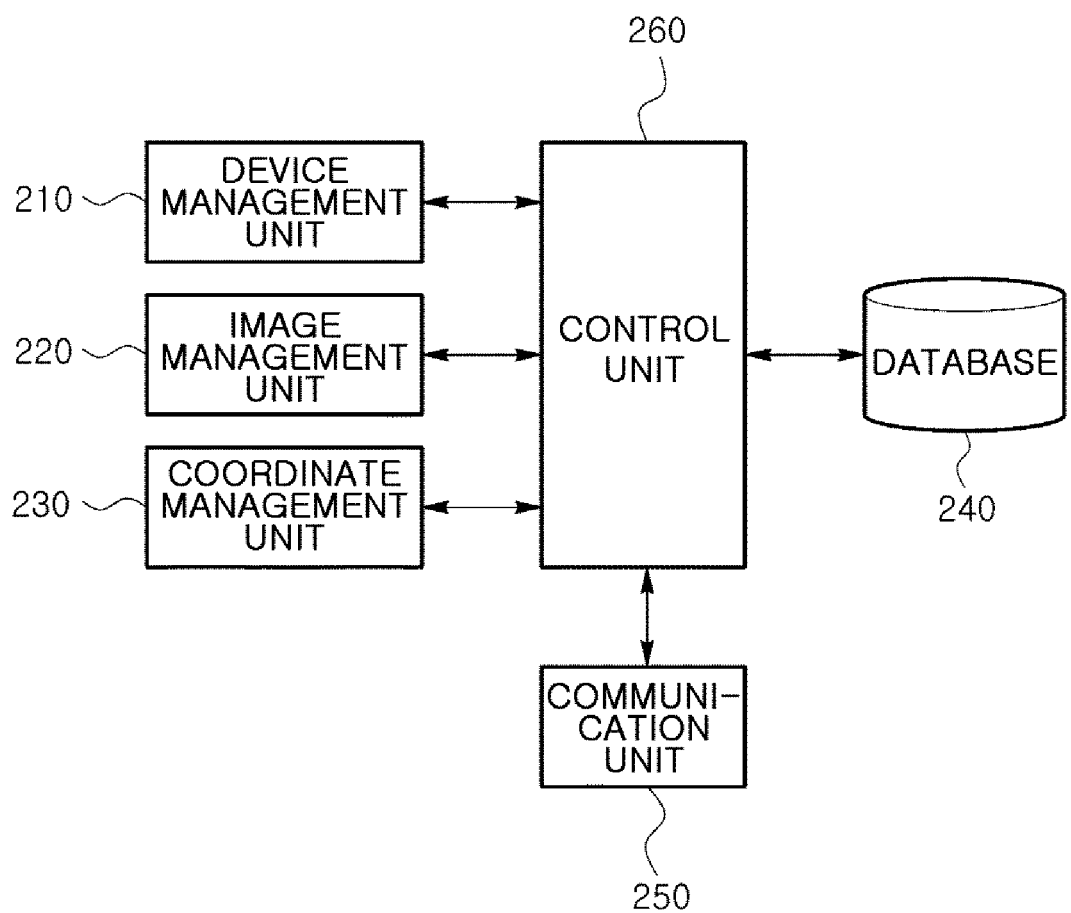
FIG. 2 is a diagram illustrating an example of an internal configuration of a monitoring system according to one embodiment of the present disclosure.

FIG. 2 is a diagram illustrating an example of an internal configuration of the monitoring system according to one embodiment of the present disclosure. Referring to FIG. 2, a monitoring system 200 may include a device management unit 210, an image management unit 220, a coordinate management unit 230, a database 240, a communication unit 250, and a control unit 260. According to the present embodiment, at least some of the device management unit 210, the image management unit 220, the coordinate management unit 230, the database 240, the communication unit 250, and the control unit 260 may be program modules communicating with an external system (not shown). These program modules may be included in the monitoring system 200 in the form of an operating system, application program modules, or other program modules and may be physically stored in various known memory devices. These program modules may also be stored in a remote storage device capable of communicating with the monitoring system 200. Alternatively, the program modules collectively include, according to the present disclosure, a routine, a subroutine, program, an object, a component, a data structure, and the like which perform a specific task or a specific abstract data type, which will described below, but the present disclosure is not limited thereto.

Although the monitoring system 200 has been described as above, this description is illustrative and it is obvious to those skilled in the art that at least some of components or functions of the monitoring system 200 may be implemented in the monitoring device 100, which is a portable device worn on a body part of the subject, as necessary, or may be included in the monitoring device 100.

First, according to the present embodiment, the device management unit 210 may perform a function of managing the plurality of optodes 110 included in the monitoring device 100 to be able to irradiate near-infrared light onto a body part (e.g., a head part) of a subject and to detect the near-infrared light reflected or scattered from the body part of the subject. Further, the device management unit 210 according to one embodiment of the present disclosure may manage other required functions or components of the monitoring device 100, which are necessary for performing monitoring on hemodynamics of the subject.

The image management unit 220 according to the present embodiment may perform a function of managing images captured in a state in which the subject wears the monitoring device 100. For example, the image management unit 220 may receive and analyze images of a front view and a side view of the subject wearing the monitoring device 100 on the head and may calculate data for a coordinate system transformation from the images of the subject so as to be able to confirm a result measured by the monitoring device 100 based on a standard space, e.g., a standard brain.

In the present embodiment, the image capturing the subject wearing the monitoring device refer to a photograph, but the present disclosure is not limited thereto. That is, in the present embodiment, the image capturing the subject captured may be sufficient as long as it has a form by which an appearance of the subject can be represented and from which a still photography can be extracted so that the image includes both not only a photograph but also other types of images such as a moving image and the like.

Meanwhile, a method of analyzing the image of the subject and calculating data for a coordinate system transformation will be described in detail below.

The coordinate management unit 230 according to the present embodiment may perform a function of transforming a local coordinate system in the monitoring device 100 into a standard coordinate system to standardize a measured result. Specifically, the coordinate management unit 230 may perform a function of transforming the local coordinate system in the monitoring device 100 into a photogrammetric coordinate system first on the basis of data calculated in the image management unit 220 and then transforming the photogrammetric coordinate system into a predetermined standard coordinate system through a predetermined transformation matrix. That is, according to the present embodiment, the coordinate management unit 230 may transform the local coordinate system in the monitoring device 100 into the standard coordinate system through a two-stage transformation on the basis of the image of the subject wearing the monitoring device 100.

In the present embodiment, a MNI coordinate system may be used as a standard coordinate system for standardizing a measured result when the monitoring device is worn on the head. The MNI coordinate system is a coordinate system based on a standard brain developed by the Montreal Neurological Institute. Using such a standard coordinate system, it is possible to compare results measured from subjects with different anatomical structures in the brain and to accumulate and utilize data. Meanwhile, in the present embodiment, the MNI coordinate system is exemplified as the standard coordinate system, but the present disclosure is not limited thereto. For example, it is possible to employ another standard coordinate system such as a Talairach coordinate system capable of representing an anatomical structure in the brain in a standardized form, or to employ a suitable standard coordinate system according to a target object when a body part other than the brain is measured.

The database 240 according to the present embodiment may store basic information on a coordinate system transformation. For example, the database 240 may store information on a local coordinate system predefined in the monitoring device 100 and information on a transformation matrix and the like so as to transform a photogrammetric coordinate system into a standard coordinate system. Further, an image of the subject used for the coordinate system transformation and information on the image, e.g., information on a position of a reference point, which will be described below, and a distance between the positions, may be calculated and stored in advance in the database 240.

In the present embodiment, the database 240 has been illustrated as being included in the monitoring system 200. However, as necessary for those skilled in the art who composes the present disclosure, the database 240 may be separately configured from the monitoring system 200. Meanwhile, the database 240 in the present disclosure is a concept including a computer-readable recording medium and may be databases including not only a database in a narrow sense but also a database in a broad sense including a data record based on a file system, and even a simple set of logs, if it is possible to retrieve and extract data, the database 240 in the present disclosure may be achieved.

The communication unit 250 according to one embodiment of the present disclosure performs a function of allowing the monitoring system 200 to communicate with an external device.

The control unit 260 performs a function of controlling a flow of data between the device management unit 210, the image management unit 220, the coordinate management unit 230, the database 240, and the communication unit 250. That is, the control unit 260 controls a flow of data from the outside or between the components of the monitoring system 200 to allow each of the device management unit 210, the image management unit 220, the coordinate management unit 230, the database 240, and the communication unit 250 to perform an inherent function.

Method of Monitoring Hemodynamics

Subsequent to the description of the monitoring system, a method of standardizing the measured result from the above-described monitoring device and monitoring hemodynamics will be described below.

Figure 3:
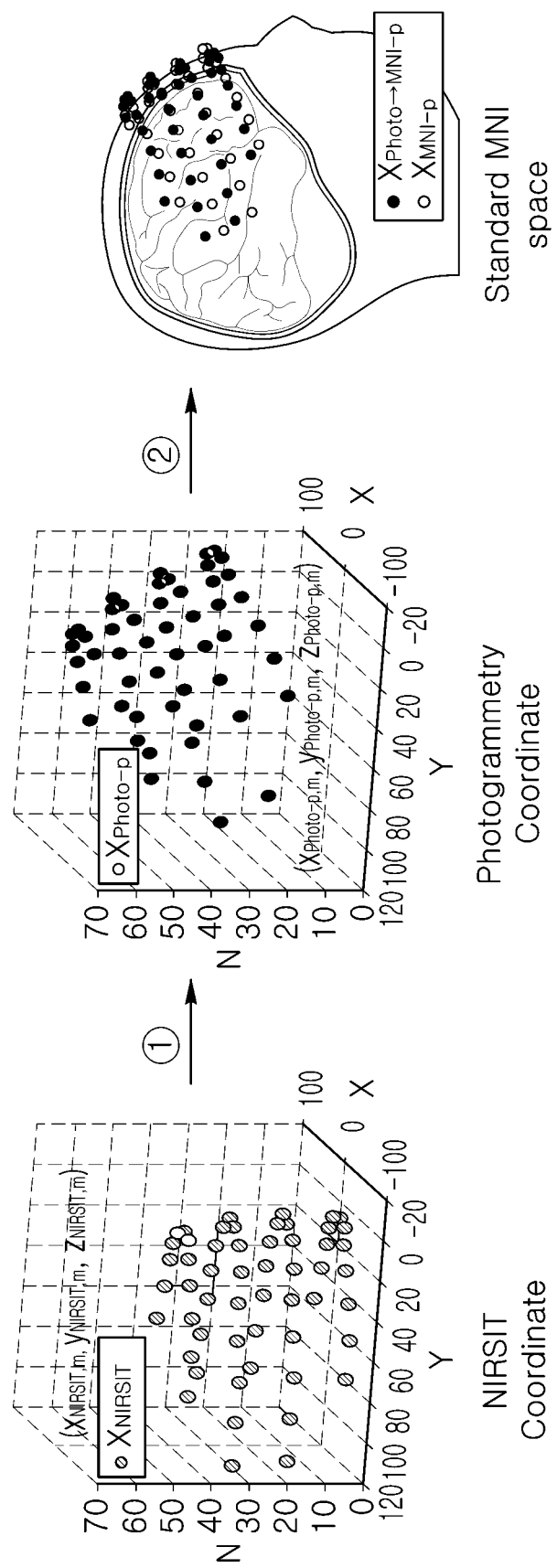
FIG. 3 is a diagram illustrating a process of standardizing results measured from the monitoring device according to one embodiment of the present disclosure.

FIG. 3 is a diagram illustrating a process of standardizing results measured from the monitoring device according to one embodiment of the present disclosure. Referring to FIG. 3, in the present embodiment, a position of an optode is transformed into a position in a standard coordinate system through two stages.

To this end, a local coordinate system is set first in the monitoring device.

Figure 4:
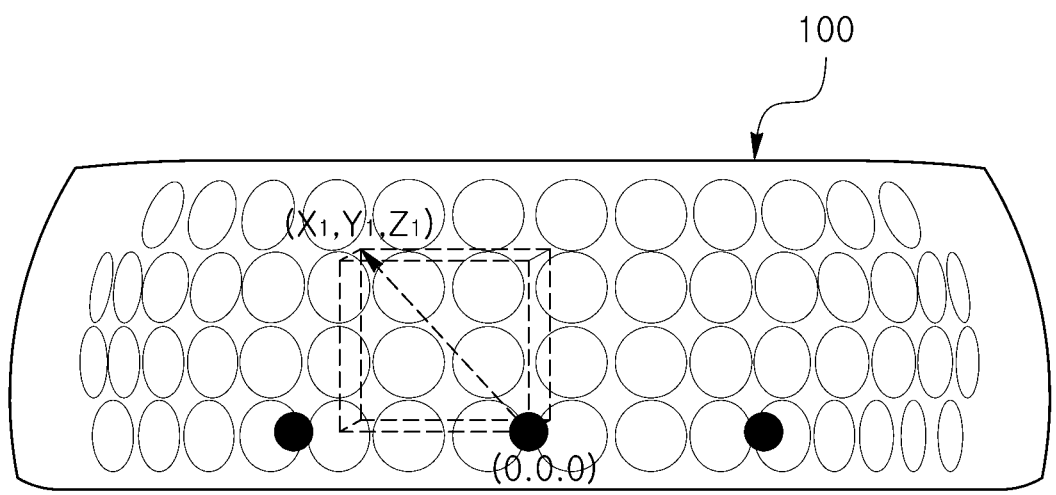
FIG. 4 is a diagram illustrating an example of a local coordinate system in the monitoring device according to one embodiment of the present disclosure.

FIG. 4 is a diagram illustrating an example of a local coordinate system in the monitoring device according to one embodiment of the present disclosure. Referring to FIG. 4, each of positions on the monitoring device may be represented on a local coordinate system by setting an orthogonal coordinate system in which a point at a central portion of the monitoring device becomes the origin. For example, a left graph of FIG. 3 shows positions of a plurality of optodes of the monitoring device on the local coordinate system that is set as described above. Consequently, the positions of the plurality of optodes of the monitoring device may be assigned to coordinates on the local coordinate system.

The local coordinate system and the coordinates of each of the optodes in the monitoring device may employ a local coordinate system and coordinates, which are predetermined to each of the monitoring devices. This information may be stored in advance in the database 240 of the above-described monitoring system 200. That is, in the present disclosure, the setting of the local coordinate system in the monitoring device includes both of a case in which, when coordinate system information is stored in advance in the monitoring device, the stored coordinate system information is directly used, and a case in which a local coordinate system is separately set during a process of processing a result measured by a monitoring device before or after obtaining an image of a subject wearing the monitoring device. Further, the local coordinate system in the monitoring device according to the present disclosure is sufficient as long as it can represent a relationship between arbitrary points on the monitoring device, and the local coordinate system is not limited by a formal name or form of the coordinate system.

Next, an image capturing the subject wearing the monitoring device on a body part (e.g., a head part) is acquired, and the local coordinate system of the monitoring device is transformed into a photogrammetric coordinate system using the captured image (see a middle graph of FIG. 3). The image of the subject image may be acquired through a camera installed at a general digital camera, a tablet, a smart phone, or the like, and any type of device may be employed as long as it can obtain an image with respect to the subject.

Figure 5:
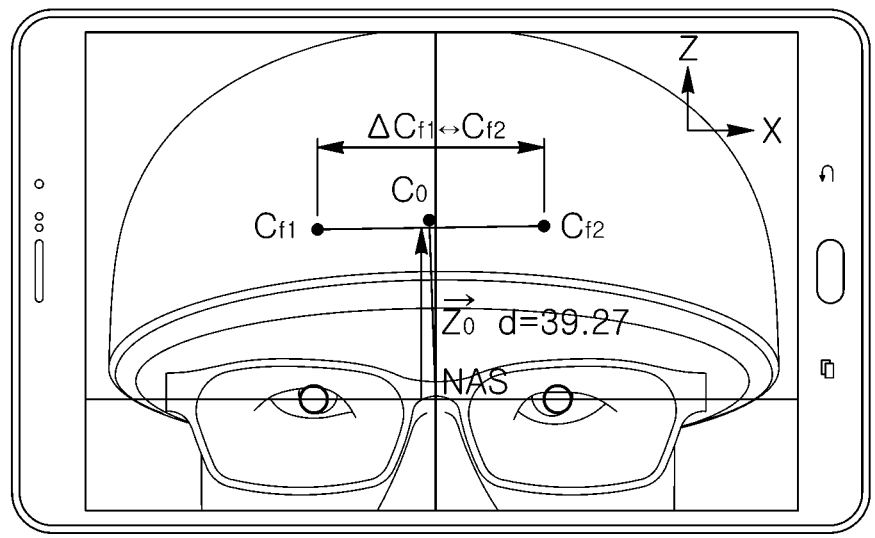
FIG. 5 is a diagram showing a relationship between a local coordinate system and a photogrammetric coordinate system of the monitoring device from images capturing a front view and a side view of a subject wearing the monitoring device according to one embodiment of the present disclosure.
Figure 5:
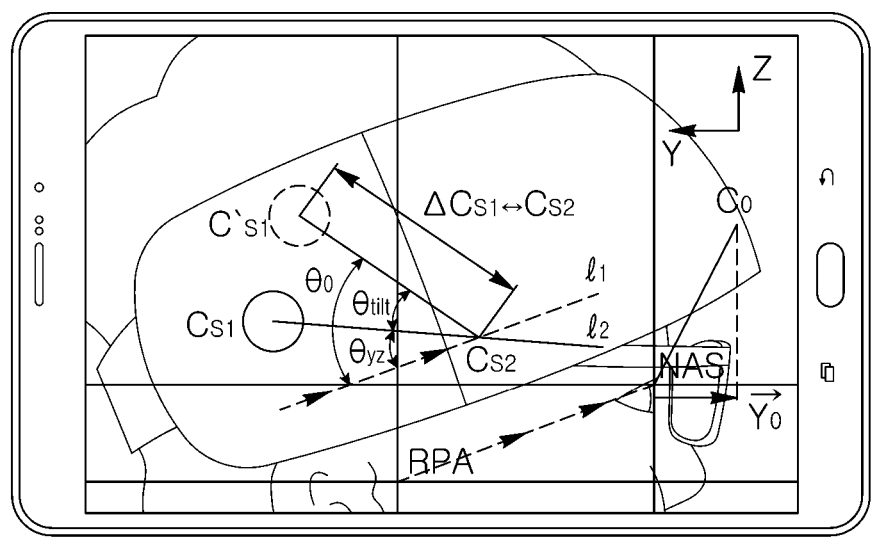

FIG. 5 is a diagram showing a relationship between the local coordinate system and the photogrammetric coordinate system of the monitoring device from images capturing a front surface and a side surface of the subject wearing the monitoring device according to one embodiment of the present disclosure. As described above, in the present embodiment, the relationship between the local coordinate system and the photogrammetric coordinate system of the monitoring device may be analyzed through the front view and the side view of the subject such that a transformation to the photogrammetric coordinate system may be performed.

Referring to FIG. 5 illustrating a case in which the monitoring device is worn on the head part, a nasion (NAS) of the subject in the front view thereof may be set as the origin of the photogrammetric coordinate system. The NAS is one of reference points on the MNI coordinate system. In the present embodiment, measurement as to where each of points of the monitoring device is located is performed about the NAS.

In the present embodiment, the photogrammetric coordinate system is transformed through parallel translation (i.e., parallel translation in y- and z-axis directions) and rotatory translation (i.e., rotatory translation about an x-axis) on the local coordinate system. For example, a transformation matrix for a linear affine transformation of the parallel translation and rotatory translation of the coordinate system may be obtained through the front and side photographs of the subject.

First, in the front view of FIG. 5, the origin (NAS) of the photogrammetric coordinate system and the origin $C_O$ of the local coordinate system of the monitoring device are placed on a straight line in a vertical direction (the z-axis direction), and thus a z-axis component of a vector from the origin (NAS) of the photogrammetric coordinate system to the origin $C_O$ of the local coordinate system may be calculated. The z-axis component may be calculated by calculating a distance between pixels by counting the number of pixels between two reference points $C_{f1}$ and $C_{f2}$ of which an actual distance therebetween is calculated in advance from the front view, counting the number of pixels between the NAS and $C_O$ in the z-axis direction on the front view, and multiplying the number of pixels between the NAS and $C_O$ by the distance between pixels, which is calculated using the two reference points. This is expressed as the following equation.

$$\vec{Z_o} = \Delta_{z,N \leftrightarrow C_o} \frac{l_{C_{f1} \leftrightarrow C_{f2}}}{\Delta_{C_{f1} \leftrightarrow C_{f2}}} \vec{a_Z} \qquad \text{[Equation 1]}$$

Here, $\vec{a_z}$ denotes a unit vector in the z-axis direction, $$\Delta_{z,N \to C_o}$$

denotes the number of pixels between the NAS and $C_O$, which is counted in the z-axis direction, $$l_{C_{f1} \leftrightarrow C_{f2}}$$

denotes a distance between the two reference points $C_{f1}$ and $C_{f2}$ located in the x-axis direction on the local coordinate system, and $$\Delta_{C_{f1} \leftrightarrow C_{f2}}$$

denotes the number of pixels between the two reference points $C_{f1}$ and $C_{f2}$ counted in the x-axis direction. Among $\vec{a_z}$, $$\Delta_{z,N \to C_o},$$

$$l_{C_{f1} \leftrightarrow C_{f2}},$$

and $$\Delta_{C_{f1} \leftrightarrow C_{f2}},$$

$$l_{C_{f1} \leftrightarrow C_{f2}}$$

which is the distance between the two reference points $C_{f1}$ and $C_{f2}$ may be calculated in advance and stored in the database 240.

Similarly, a y-axis component of a vector from the origin (NAS) of the photogrammetric coordinate system to the origin $C_O$ of the local coordinate system may be calculated from the side view of FIG. 5. The y-axis component may be calculated by calculating a distance between pixels by counting the number of pixels between two reference points $C_{s1}$ and $C_{s2}$ of which an actual distance between the two reference points $C_{f1}$ and $C_{f2}$ is known on the side view, counting the number of pixels between the NAS and $C_O$ in the y-axis direction on the front view, and multiplying the number of pixels between the NAS and $C_0$ by the distance between pixels, which is calculated using the two reference points. This is expressed as the following equation.

$$\vec{y_0} = \Delta_{y,N \leftrightarrow C_0} \frac{l_{C_{s1} \leftrightarrow C_{s2}}}{\Delta_{C_{s1} \leftrightarrow C_{s2}}} \vec{a_y} \quad \text{[Equation 2]}$$

Here, denotes a unit vector in the y-axis direction, denotes the number of pixels between the NAS and $C_0$, which is counted in the y-axis direction, denotes a distance between the two reference points $C_{s1}$ and $C_{s2}$ on the local coordinate system, and denotes the number of pixels between the two reference points $C_{s1}$ and $C_{s2}$.

Next, a rotation angle of the local coordinate system of the monitoring device about the x-axis may be calculated from the side view of the subject.

Referring to the side view of FIG. 5, the rotation angle of the local coordinate system about the x-axis may be obtained by measuring an angle between a straight line connecting the NAS to a right pre-auricular point (RPA) and a straight line connecting the two reference points $C_{s1}$ and $C_{s2}$.

Specifically, when assuming a straight line $l_1$ passing the reference point $C_{s2}$ and being parallel to a straight line connecting the NAS and the RPA in the monitoring device, an angle $\theta_0$ between the straight line $l_1$ and a straight line connecting the reference point $C_{s2}$ and a reference point $C'_{s1}$ which is a reference point before the monitoring device is worn is calculated, an angle $\theta_{yz}$ between the straight line $l_1$ and a straight line connecting the reference point $C_{s2}$ and the reference point $C_{s1}$ (i.e., at which $C_{s1}$ is rotationally transformed) which is a reference point after the monitoring device is worn is calculated, and then an angle $\theta_{tilt}$ for which the local coordinate system is rotated about the x-axis may be calculated from the angles $\theta_0$ and $\theta_{yz}$. This is expressed as the following equation.

$$\theta_{tilt} = \theta_0 - \theta_{yz} \quad \text{[Equation 3]}$$

Here, the angle $\theta_0$ between the straight line $l_1$ and a straight line connecting the reference point $C_{s2}$ and the reference point $C'_{s1}$ which is a reference point before the monitoring device is worn may be calculated in advance and stored in the database 240.

As described above, when a parallel translation component $y_0$ and $z_0$ in the y- and z-axis directions and the rotatory translation component $\theta_{tilt}$ about the x-axis, transformation of a coordinate $X_{NIRSIT}$ in the local coordinate system of the monitoring device into a coordinate $X_{photo-p}$ in the local coordinate system may be expressed as follows.

$$X_{photo-p,m} = \begin{bmatrix} x_{photo-p,m} \\ y_{photo-p,m} \\ z_{photo-p,m} \\ 1 \end{bmatrix} = \begin{bmatrix} 1 & 0 & 0 & 0 \\ 0 & \cos\theta_{tilt} & -\sin\theta_{tilt} & y_0 \\ 0 & \sin\theta_{tilt} & \cos\theta_{tilt} & z_0 \\ 0 & 0 & 0 & 1 \end{bmatrix} \begin{bmatrix} x_{NIRSIT,m} \\ y_{NIRSIT,m} \\ z_{NIRSIT,m} \\ 1 \end{bmatrix} \quad \text{[Equation 4]}$$

Meanwhile, in the present embodiment, the transformation matrix to the photogrammetric coordinate system is calculated using the front view and the side view (a photograph of a right surface) of the subject wearing the monitoring device, but the present disclosure is not limited thereto, and it is also possible to use two or more photographs captured in different directions. In this case, however, it is possible to increase accuracy of coordinate transformation by utilizing two photographs perpendicular to each other.

Further, the origin in the setting of the photogrammetric coordinate system is not limited to the NAS, another point such as an RPA, a left pre-auricular point (LPA), or the like, which one of reference points used in magnetic resonance imaging (MRI), may become the origin, and an arbitrary point on a face in the image of the subject may become the origin.

When the transformation from the local coordinate system of the monitoring device to the photogrammetric coordinate system is made, the photogrammetric coordinate system is transformed again to the standard coordinate system (see a right drawing of FIG. 3). That is, a process of moving a specific location on the monitoring device worn by the subject onto a standardized space (e.g., an MNI space) is performed.

Figure 6:
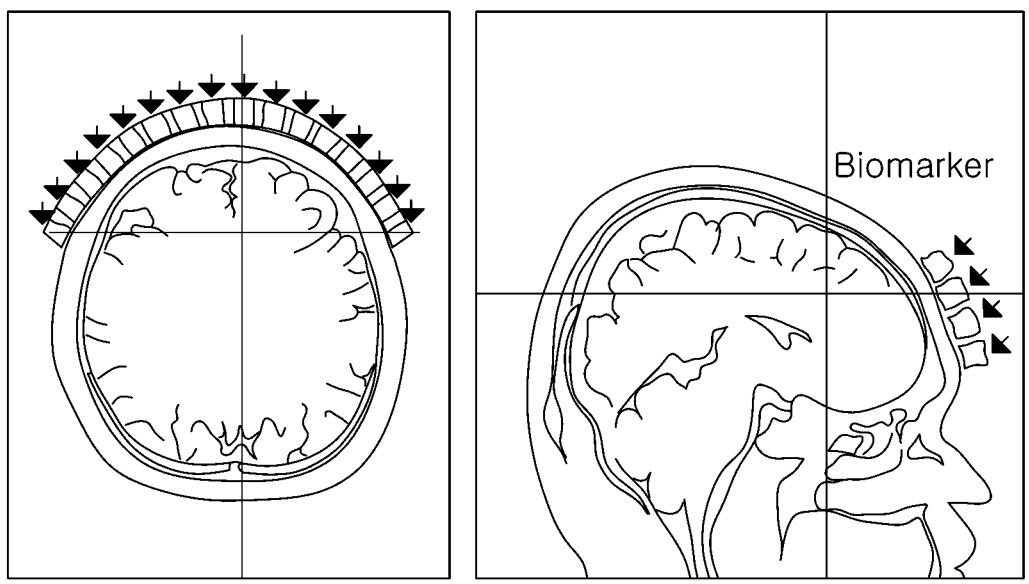
FIG. 6 is a diagram illustrating an example of a process of transforming a photogrammetric coordinate system to a standard coordinate system according to one embodiment of the present disclosure.

FIG. 6 is a diagram illustrating an example of a process of transforming a photogrammetric coordinate system to a standard coordinate system according to one embodiment of the present disclosure. Referring to FIG. 6, a photogrammetric coordinate system may be transformed into a standard coordinate system, e.g., the MNI coordinate system, through affine transformation. This may be expressed as the following equation.

$$X_{photo \rightarrow MNI-p} = M_{AT,ave} * X_{photo-p}$$

Here, an affine transformation matrix $M_{AT,ave}$ for transforming the photogrammetric coordinate system into the standard coordinate system may be obtained through an MRI scan of different subjects in advance and may be stored in advance in the database 240 of the monitoring system 200.

As described above, according to the monitoring method of one embodiment of the present disclosure, data measured from the monitoring device using an image for which the subject wears the monitoring device may be mapped to a standard space, e.g., a standard coordinate system based on a standard brain. Therefore, it is possible to directly compare the results measured from different subjects on the standard coordinate system such that evaluation of the measured results can be easily performed. Further, it is possible to standardize and accumulate the results obtained through the monitoring device such that the results can be utilized for big data analysis in the future.

In the foregoing description, although the head part (i.e., the brain) has been mainly described as being the body part which is a monitoring target, a body part which will be target of the monitoring according to the present disclosure is not necessarily limited to the head part. It is noted that any other body parts, which can be monitored on the basis of hemodynamics, can considered as targets of the monitoring according to the present disclosure.

The above-described embodiments according to the present disclosure may be implemented in the form of a program command which is executable through various computer components and may be recorded in a non-transitory computer-readable recording medium. The non-transitory computer-readable recording medium may include program commands, data files, data structures, and the like alone or a combination thereof. The program commands recorded in the non-transitory computer-readable recording medium may be specially designed and configured for the present disclosure or may be available to those skilled in the computer software. Examples of the non-transitory computer-readable recording media include magnetic media such as a hard disk, a floppy disk, and a magnetic tape, optical recording media such as a compact disc read only memory (CD-ROM) and a digital versatile disc (DVD), magneto-optical media such as a floptical disk and the like, and hardware devices specifically configured to store and execute program commands, such as a read only memory (ROM), a random access memory (RAM), a flash memory, and the like. Examples of the program instructions include machine language codes generated by a compiler, as well as high-level language codes which are executable by a computer using an interpreter or the like. The above-described hardware devices may be configured to operate as one or more software modules so as to perform a process of the present disclosure, and vice versa.

While the present disclosure has been described with reference to specific items such as particular components, exemplary embodiments, and drawings, these are merely provided to help understanding the present disclosure, and the present disclosure is not limited to these embodiments, and those skilled in the art to which the present disclosure pertains can variously alter and modify from the description of the present disclosure.

Therefore, the spirit of the present disclosure should not be limited to the above-described embodiments, and it should be construed that the appended claims as well as all equivalents or equivalent modifications of the appended claims will fall within the scope of the present disclosure.

What is claimed is:

1. A method for standardizing a measured result obtained from a device for monitoring hemodynamics, the method comprising:
    capturing images of a subject wearing a monitoring device in two different directions;
    defining a photogrammetric coordinate system on the basis of the captured images and transforming a predetermined local coordinate system of the monitoring device into the photogrammetric coordinate system; and
    transforming the photogrammetric coordinate system into a standard coordinate system based on a standard space using a predetermined affine transformation matrix,
    wherein the transforming of the local coordinate system into the photogrammetric coordinate system comprises calculating amounts of parallel translation and rotatory translation between the local coordinate system and the photogrammetric coordinate system in the captured images, and obtaining a transformation matrix for transforming the local coordinate system into the photogrammetric coordinate system, using predetermined reference points of the monitoring device.

2. The method of claim 1, wherein the two directions are perpendicular to each other.

3. The method of claim 1, wherein an origin of the photogrammetric coordinate system is set to an arbitrary point on a face of the subject in the images of the subject.

4. The method of claim 3, wherein the origin of the photogrammetric coordinate system is set to any one of a nasion (NAS), a right pre-auricular point (RPA), and a left pre-auricular point (LPA).

5. A non-transitory computer-readable recording medium for recording a computer program for performing the method according claim 1.

6. A system for standardizing a measured result obtained from a device for monitoring hemodynamics, the system comprising:
    an image management unit configured to receive and analyze images of a subject wearing a monitoring device, which are captured in two different directions; and
    a coordinate management unit configured to map a measurement result of the monitoring device to a standard coordinate system based on a standard space, by transforming a local coordinate system of the monitoring device into a photogrammetric coordinate system on the basis of the images analyzed in the image management unit, and transforming the photogrammetric coordinate system into the standard coordinate system using a predetermined affine transformation matrix,
    wherein the coordinate management unit is configured to calculate amounts of parallel translation and rotatory translation between the local coordinate system and the photogrammetric coordinate system in the images, and obtain a transformation matrix for transforming the local coordinate system into the photogrammetric coordinate system, using predetermined reference points of the monitoring device.

7. The system of claim 6, wherein the two directions are perpendicular to each other.

8. The system of claim 6, wherein the coordinate management unit is configured to set an origin of the photogrammetric coordinate system to an arbitrary point on a face of the subject in the images of the subject.

9. The system of claim 8, wherein the coordinate management unit is configured to set the origin of the photogrammetric coordinate system to any one of a nasion (NAS), a right pre-auricular point (RPA), and a left pre-auricular point (LPA).

* * * * *